US008426124B2

(12) United States Patent
Reiter et al.

(10) Patent No.: US 8,426,124 B2
(45) Date of Patent: Apr. 23, 2013

(54) TWO-STEP TEMPERATURE PROFILE FOR THE PROPAGATION OF VIRUSES

(75) Inventors: Manfred Reiter, Vienna (AT); Leopold Grillberger, Vienna (AT); Wolfgang Mundt, Vienna (AT)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

(21) Appl. No.: 12/112,261

(22) Filed: Apr. 30, 2008

(65) Prior Publication Data

US 2008/0286307 A1 Nov. 20, 2008

Related U.S. Application Data

(60) Provisional application No. 60/927,693, filed on May 4, 2007.

(51) Int. Cl.
*C12Q 1/70* (2006.01)
*C12P 21/00* (2006.01)
*A61K 48/00* (2006.01)

(52) U.S. Cl.
USPC ............ 435/5; 435/91.1; 435/70.1; 424/204.1

(58) Field of Classification Search .................. None
See application file for complete search history.

(56) References Cited

U.S. PATENT DOCUMENTS

| 4,301,249 | A | * | 11/1981 | Markus et al. | 435/235.1 |
| 6,048,537 | A | * | 4/2000 | Violay et al. | 424/209.1 |
| 6,855,535 | B2 | * | 2/2005 | Meyer et al. | 435/235.1 |
| 6,951,752 | B2 | * | 10/2005 | Reiter et al. | 435/235.1 |

FOREIGN PATENT DOCUMENTS

| DE | 1526172 A1 | * | 4/2005 |
| EP | 1526172 A1 | | 4/2005 |
| WO | WO-03/085138 A1 | | 10/2003 |

OTHER PUBLICATIONS

Yuk et al. (Cytotechnology, 2006, vol. 51, p. 183-192 in IDS on Sep. 13, 2011).*
Jardon et al., pH, pCO2, and temperature effect on R-adenovirus production. *Biotechnol. Prog.*, 19(1): 202-8 (2003).
McTAGGART et al., Effects of culture parameters on the production of retroviral vectors by a human packaging cell line. *Biotechnol. Prog.*, 16(5): 859-65 (2000).
Rott et al., Biochemical studies on influenza virus multiplication at reduced temperatuers fowl plague virus chick embryo fibroblasts. *J. Gen. Virol.*, 3(part 2): 239-524 (1968).
Wechuck et al., Effect of temperature, medium composition, and cell passage on production of herpes-based viral vectors. *Biotechnol. Bioengin.* 79(1): 112-9 (2002).
Yuk et al., A serum-free vero production platform for a chimeric virus vaccine candidate. *Cytotechnol.*, 51(3): 183-92 (2006).

* cited by examiner

*Primary Examiner* — Agnieszka Boesen
(74) *Attorney, Agent, or Firm* — Marshall, Gerstein & Borun LLP

(57) ABSTRACT

The present invention provides a method for the production of a virus. The method includes providing a host cell that has been infected by the virus and cultivating the infected host cell at two different temperatures. The virus produced by the cultivation steps is subsequently collected. By using the dual temperature cultivation process, high titer and improved purity can be obtained.

25 Claims, 12 Drawing Sheets

RRV 37°C I-54

FIG. 2A

RRV 37°C I-66

FIG. 2B

RRV 37°C I-78

FIG. 2C

RRV 37°C I-90

TWO-STEP TEMPERATURE PROFILE FOR THE PROPAGATION OF VIRUSES

This application claims the benefit of priority to U.S. Provisional Application No. 60/927,693, filed May 4, 2007, the contents of which are hereby incorporated by reference in their entirety.

FIELD OF THE INVENTION

The present invention relates to the field of virus propagation.

BACKGROUND OF THE INVENTION

Virus propagation in animal cell cultures is carried out under temperature conditions that depend on the characteristics of the virus and the host system for propagation. Certain temperatures are selected for the growth of the cells (in cell culture or breeding of embryonic eggs), followed by a selected temperature for the propagation of the virus. In most cases, the virus propagation temperature is lower than the cell propagation temperature. Temperature-sensitive virus propagation relates to influencing the speed of virus propagation and the formation of antigens in a temperature range approximately centered around 20° C. for insect cell cultures (with e.g. Baculovirus production) and at temperatures up to about 37° C. for virus production in mammalian cell culture, with specific optima for each virus/host cell combination. A higher temperature affects both the infection kinetics and viral stability. When viruses are propagated at a temperature of 37° C., a decreased viral titer and lower quality of viral antigen is often observed during the latter periods of viral replication. This effect can have detrimental consequences for large scale virus propagation for vaccine production.

It is a goal of the present invention to provide improved growth conditions which do not affect the quality of the produced antigens for vaccination purposes.

SUMMARY OF THE INVENTION

The present invention provides a method for the production of a virus, wherein one or more host cells are infected by the virus and then cultivated at a first temperature (e.g., at a temperature from 31° C. to 37° C. for 1 to 48 hours) and subsequently cultivated at a second temperature which is decreased compared to the first temperature (e.g., by 1° C. to 6° C.). The virus produced by these cultivation steps is then collected.

It was now surprisingly found that for many viruses, including influenza (Orthomyxoviridae), Ross River Virus (Alphaviridae) and West Nile Virus (Flaviviridae,) cultivation conditions can be substantially improved by using a two temperature profile. A higher temperature is applied for the first phase of the virus propagation, which accelerates the formation of infectious virus particles. In a second phase, a lower temperature is applied to maintain the initial high titer obtained in the higher temperature propagation period and to allow the formation of stable antigen which may be used for further manufacturing of immunogenic vaccines.

BRIEF DESCRIPTION OF THE FIGURES

FIG. 2: NaBr plot of Ross River Virus infection at 37° C. at various time points after infection.

DETAILED DESCRIPTION OF THE INVENTION

Figure 1A:
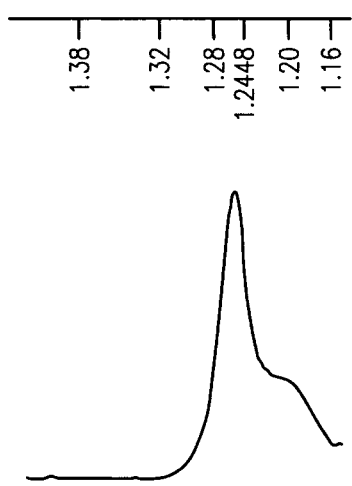
FIG. 1: Antigen banding pattern of New Caledonia virus propagated in Vero cells at (A) 32° C. and (B) 36° C.

One aspect of the invention is the realization that the two step temperature profile as described herein allows independent optimization and control of (1) the formation of active virus for multi-cycle infection of host cells, (2) the maintenance of the high titer obtained in the latter phase of replication, and (3) the antigen formation in the later phase of the production process.

In a preferred embodiment of the present invention said virus is an orthomyxovirus, alphavirus or flavivirus.

Preferably the virus is an influenza virus, and in certain embodiments is selected from the group consisting of influenza A and B, a Ross River virus and a West Nile Virus. While the examples provided herein illustrate improved antigen production for these viruses using the inventive two-temperature method, non-limiting examples of other viruses contemplated by the invention include viruses selected from the group of RNA virus families such as Reoviridae, Picornaviridae, Caliciviridae, Togaviridae, Arenaviridae, Retroviridae, Flaviviridae, Orthomyxoviridae, Paramyxoviridae, Bunyaviridae, Rhabdoviridae, Filoviridae, Coronaviridae, Astroviridae, or Bornaviridae, and DNA virus families such as Adenoviridae, Papovaviridae, Parvoviridae, Herpesviridae, Poxviridae, or Hepadnaviridae. In certain embodiments, the viruses are selected from the group consisting of Influenza A/Panama/2007/99, A/New Caledonia/20/99, B/Shangdong/7/97, B/Malaysia/2506/2004, A/Hiroshima/52/2005, and A/Solomon Islands/3/2006.

The virus can be produced in any cells suitable for the production of viruses. Preferably, the cells are of an animal cell culture or cell line. Such cells may be from a specific tissue or embryonic cells. The animal is preferably a mammal or a bird. Various embodiments of the invention may utilize canine cell lines, rodent cell lines, avian cell lines or primate tissue cell lines. For instance, in certain embodiments the cells may be MDCK cells, CHO cells, perC6 cells, HEK 293 cells, or other cells commonly used in viral propagation. In some specific embodiments the cells are epithelial cells, in particular kidney epithelial cells, such as Vero cells of an African green monkey.

In certain embodiments of the invention, the cells are cultured in a medium that does not contain animal serum proteins. Such media do not include, for example, bovine serum, or portions thereof, such as foetal bovine serum. Such media are referred to as "serum protein free media." During the viral propagation period, proteases which are required for viral propagation, such as trypsin, may be added to the media. In some embodiments, such proteases may be derived from non-animal sources such as bacterium or recombinant sources, or may be derived from animal sources. Such supplemented media are still considered to be serum protein free media within the meaning of the term as used herein.

In preferred embodiments of the invention, the methods of the invention are carried out at an industrial scale. In some embodiments of the invention, the methods are carried out in more than 50 liters of cell culture, fifty to 100 liters of cell culture, 100 to 500 liters of cell culture, 500 to 1000 liters of cell culture, or more than 1000 liters of cell culture (e.g., in 6000 liter, 10,000 liter, or even larger bioreactors). In some embodiments of the invention the methods of the invention are carried out in a stirred tank bioreactor.

In the preferred methods of the invention, the first virus propagation temperature is less than the cell culture propagation temperature for the given host cell type. In some embodiments the first temperature is between 32° C. to 37° C., preferably between 33° C. to 36° C., more preferably between 34° C. to 35.5° C., and in particular 35° C. In other embodiments, the first temperature is between 30° C. to 36° C., preferably between 30° C. to 35° C., more preferably between 31° C. to 35° C., more preferably between 31° C. to 34° C., more preferably between 32° C. to 34° C., more preferably between 32° C. to 33.5° C., even more preferably between 33° C. and 34° C., and most preferably 33.5° C., or in some embodiments, 33° C. In particular, for larger cell culture volumes (1000 liter and larger,) the lower first temperature ranges may be preferred. The first temperature may be at least 30° C., 31° C., 32° C., 33° C., 34° C., 35° C., or 36° C. or less than 38° C., 37.5° C., 37° C., 36° C., 35.5° C., or 35° C. The cultivation of the cells at the first temperature can be for more than 1, 2, 4, 6, 8, 10, 12, 14, 16, 18, 20, 22, 24, 26, 28 or 30 hours or for less than 60, 58, 56, 54, 52, 50, 48, 46, 44, 42, 40, 38, 36, 34, 32, 30, 28, 26, 24, 22, 20, 18, 16, 14 or 12 hours.

In additional embodiments, the second temperature is decreased by 1.5° C. to 5° C., preferably decreased by 2° C. to 4° C., more preferably by 2.5° C. to 3.5° C., and most preferably by 3° C. compared to the first temperature. The decrease may be by at least 1° C., 2° C., 2.5° C., 3° C., or 4° C. or by less than 6° C., 5° C., 4° C., 3.5° C., 3° C., 2.5°, or 2° C.

In other embodiments the second temperature ranges from 29° C. to 35° C., preferably from 30° C. to 34° C., more preferably from 31° C. to 33° C., more preferably from 31.5° C. to 32.5° C., and most preferably is 32° C. The second temperature may be above 28° C., 29° C., 30° C., or 31° C. or below 35° C., 34° C., 33° C., or 32° C.

This method can also be used for the production of virus antigens. Therefore, in a further aspect, the present invention provides a method for the production of a virus or viral antigens, wherein a virus is produced as described herein and the virus or viral antigens are isolated. The isolation can be performed using standard procedures to isolate and to optionally purify by decomposing the cells or harvesting cellular supernatant and then isolating the antigens (e.g. centrifugation or chromatography).

In further embodiments, the virus is fragmented or inactivated before or after the purification (e.g., according to the methods presented in WO 05/11800). Additionally, a vaccine of the virus may be prepared. A vaccine is an immunogenic composition of an antigenic substance, where the antigenic substance can be the non-infectious virus, its hull, particles or its antigens. When a vaccine is administered, it results in the immunization in a host, (e.g. a mammal such as a human or a bird). The vaccination may cause a specific reaction to the vaccine and some minor inflammation, but generally the response to vaccination is greatly reduced compared to the response to an infection caused by a fully viable virus.

The present invention is further illustrated by the following examples, which are merely exemplary and are not meant to limit the invention in any way.

EXAMPLES

Many viral membrane proteins require post-translational modification to produce replication-competent viruses. In Influenza viruses, proteolytic cleavage of the precursor hemagglutinin (HA) molecule (HA0) into HA1 and HA2 subunits, which generates a fusogenic domain at the amino terminal region of the HA2, is essential for entry of the virus into cells. Therefore the initiation of the infectious cycle in a cell culture has to be catalyzed by the addition of a protease. For the vaccine manufacturing process gamma irradiated trypsin from porcine origin is used.

The conventional temperature profile for influenza growth in cell cultures, such as Vero cells, is one where the temperature is constant at e.g. 33° C. (for B-strains) to 37° C. (for A-strains). [see, e.g., Govorkava E A et al. Journal of Virology, Vol. 70, Nr. 8, August 1996, p. 5519-5524]. An aspect of this invention is the realization, through small scale experiments in 10 L bioreactor systems, that elevated temperature profiles during the initial infectious phase can have a positive effect on the overall cycle time of a influenza production process. In addition, a positive effect on antigen purity measured as Vero protein/SRD ratio could be obtained. To prove this concept, 100 L scale experiments were carried out, as described herein.

Example 1

Influenza A/New Caledonia/20/99 Production at 32 and 36° C.

Vero cultures of bioreactor runs at 32° C. and at 36° C. were infected with the A/New Caledonia/20/99 virus. The set parameters for pH, pO$_2$, cell density and trypsin amount added to the culture were comparable and reflected the large scale conditions for the manufacturing of Influenza antigen. The effect of increased temperature on virus yield and cycle time is compared in Table 1.

TABLE 1

Comparison of HA and residual oxygen uptake rate("residual OUR") compared to day 0 of the infectious cycle*).

| Temp. | HA day 2 (2$^n$ HAU/50 μL) | HA day 3 (2$^n$ HAU/50 μL) | Res. OUR (%)* day 2 | Res. OUR (%)* day 3 |
|---|---|---|---|---|
| 32° C. | 6 | 8 | 80 | 50 |
| 36° C. | 7 | 8 | 20 | <5 |

After two days, a residual oxygen uptake rate of 20% was observed for the 36° C. culture, which fell below 5% by day 3. The propagation of influenza virus at 36° C. resulted in high infectivity and thus reduction of the total culture time compared to the 32° C. conditions. To the contrary, the 32° C. culture resulted in higher residual OURs of 80% and 50% respectively on day 2 and day 3. The final HA titers were comparable. However, from antigen separation experiments by ultracentrifugation with a NaBr gradient, an antigenic shift of the banding pattern occurred under the 36° C. conditions at culture day 3 (FIG. 1B), whereas the elution profile measured by the UV 254 nm detector resulted in a comparably high but more symmetric peak for the 32° C. culture (FIG. 1A). In terms of product yield and especially purity the 36° C. conditions may therefore have several disadvantages.

Figure 1B:
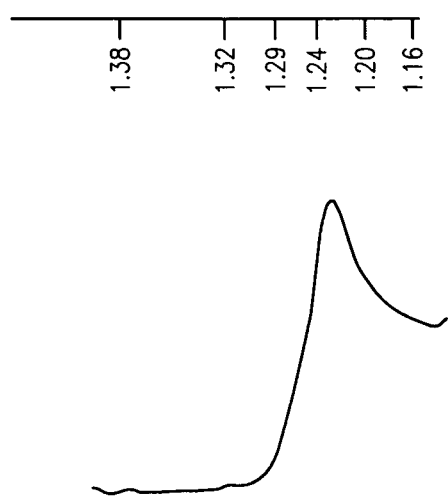
Figure 3A:
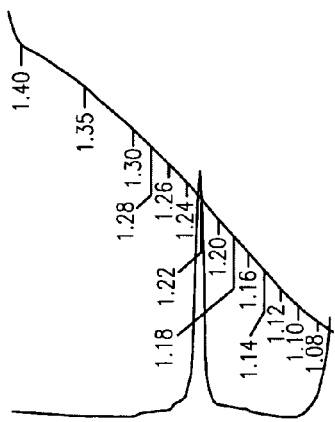
FIG. 3: NaBr plot of Ross River Virus infection at 35° C. at various time points after infection.
Figure 3B:
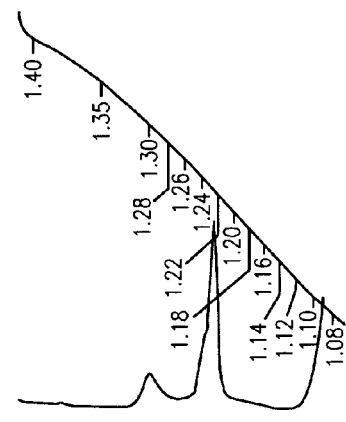
Figure 3C:
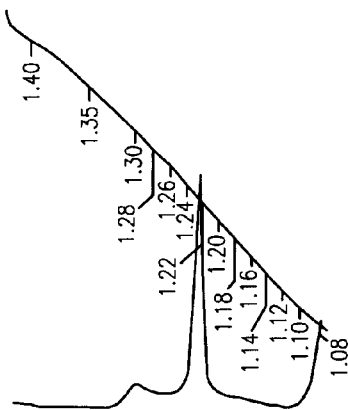
Figure 3D:
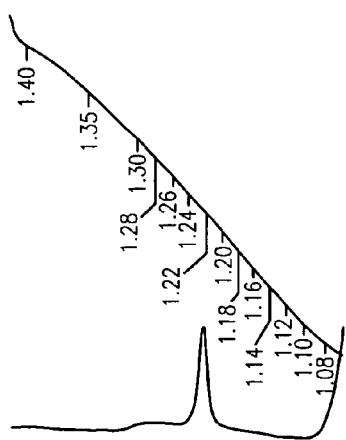
Figure 4A:
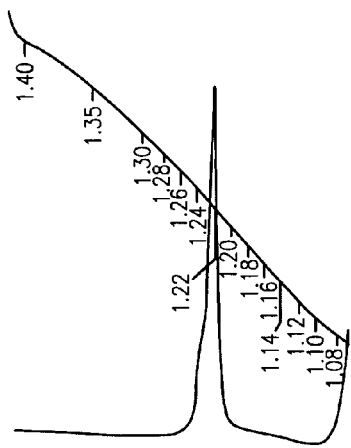
FIG. 4: NaBr plot of Ross River Virus infection at 32° C. at various time points after infection.
Figure 4B:
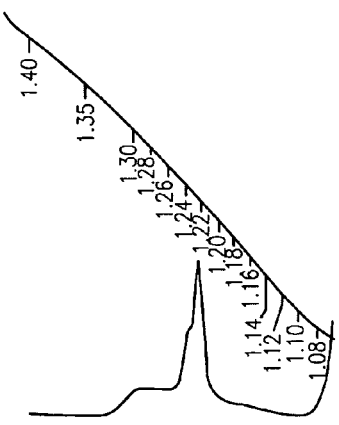
Figure 4C:
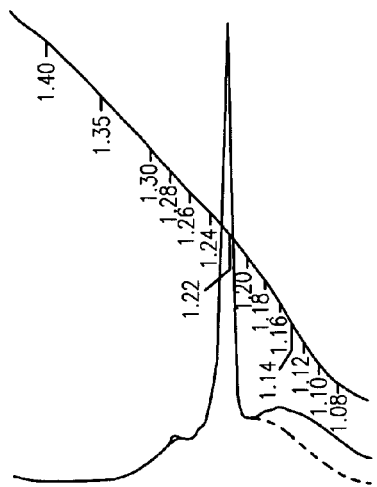
Figure 4D:
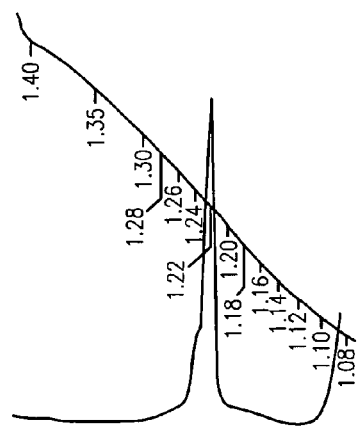
Figure 5A:
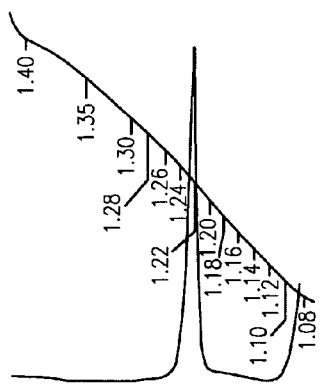
FIG. 5: NaBr plot of Ross River Virus infection at 35° C./32° C. at various time points after infection.
Figure 5B:
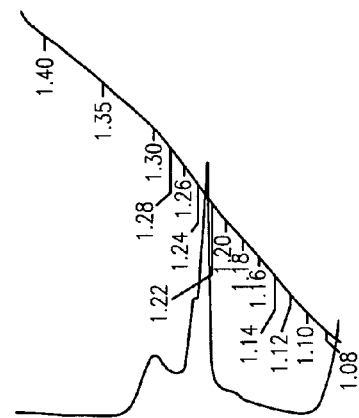
Figure 5C:
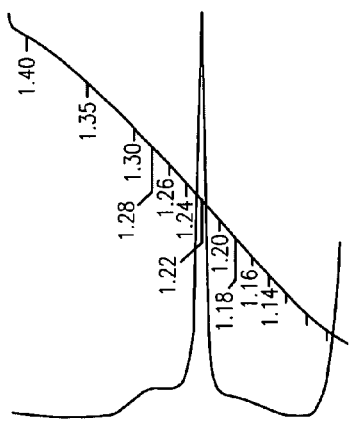
Figure 5D:
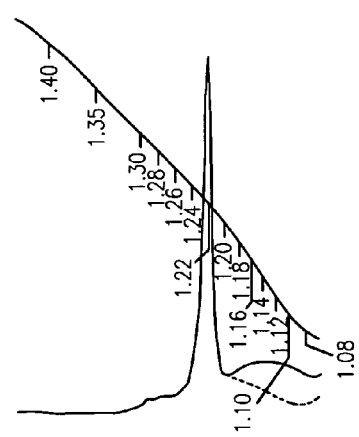

For the current production process virus antigen is harvested from a sucrose gradient. For the 36° C. experiment it can therefore be concluded that part of the antigen is shifting to the low density fraction (FIG. 1B).

Example 2

Influenza A/Panama/2007/99 Production at 32, 33, and 34° C.

To investigate the effect of increased cultivation temperature on Panama virus yield and cycle time, three 10 L bioreactor systems were operated in parallel with temperatures set at 32° C., 33° C. and 34° C. respectively. All other parameters set points were comparable to the experiments described under Example 1.

In Table 2, the process cycle time of the three bioreactor systems are given. The cultures were terminated after reaching 20% residual oxygen uptake rate (80% reduction in metabolic oxygen consumption), and kinetics of the infectious cycle were compared. For the 34° C. experiment a cycle time reduction of 21 hrs could be achieved.

TABLE 2

Comparison of process time required to reach 20% residual OUR (compared to day 0 of the infectious cycle) as a function of process temperature.

| Temperature | Process Time to reach 20% residual OUR (hrs) |
|---|---|
| 32° C. | 90 |
| 33° C. | 79 |
| 34° C. | 69 |

The culture supernatants were centrifuged, treated with Benzonase and formalin according to standard protocols. The inactivated harvests (MVHS) were purified by sucrose gradient ultracentrifugation (see Table 3).

TABLE 3

Comparison of Influenza A/Panama/2007/99 antigen yield, SRD/protein ratio and Vero-protein impurity obtained from sucrose-gradient-purified virus from the temperature experiments.

| Production conditions | Yield (mg SRD) | SRD/Protein ratio (mg/mg) | Vero-protein/SRD ratio (mg/mg) |
|---|---|---|---|
| 32° C. | 13.8 | 0.79 | 0.25 |
| 33° C. | 12.2 | 0.70 | 0.38 |
| 34° C. | 12.4 | 0.67 | 0.45 |

From Table 2, it can be concluded that elevated temperature conditions resulted in a reduced cycle time. However, as shown in Table 3, elevated temperature conditions (e.g., 33° C. and 34° C.) had a negative effect on the overall virus antigen yield and the quality of the purified virus, as evidenced by both the SRD/protein ratio and Vero-protein/SRI ratio. Therefore a reduced purity of the virus antigen at higher temperatures was observed.

Example 3

Influenza A/New Caledonia/20/99 Production with Early Virus Amplification at 35° C.

This example concerns culture experiments with an increased temperature set for the first 24 hours of the Influenza virus production process. Vero cell cultures were infected with A/New Caledonia/20/99 virus at the 100 liter scale.

A comparison of the conventional temperature profile (i.e., a 32° C. temperature set point throughout the entire fermentation process) and the modified processing with early virus amplification at 35° C. was done. This new process was characterized by initial virus replication at 35° C. for 24 hours post infection (p.i.), followed by a incubation at 32° C. until 91 hrs. p.i. In Table 4, a comparison of Influenza A/New Caledonia/20/99 antigen purity (SRD/protein ratio) and Vero-protein impurity of the sucrose gradient purified virus from the 100 liter scale runs is given.

TABLE 4

Comparison of Influenza A/New Caledonia/20/99 antigen purity (SRD/protein ratio) and Vero-protein impurity as a function of different temperature profiles. The virus was purified from temperature experiments using a sucrose gradient.

| Production conditions | Yield (mg SRD/ L harvest) | SRD/Protein Ratio (mg/mg) | Vero-protein/SRD Ratio (mg/mg) |
|---|---|---|---|
| 32° C. until 95 hrs. p.i. | 1.4 | 0.24 | 0.59 |
| 35° C. until 24 hrs. p.i./ 32° C. until 91 hrs. p.i. | 1.3 | 0.32 | 0.29 |

This data clearly demonstrated that a temperature set of 35° C. for the first 24 hours of the fermentation process had a positive effect not only on the SRD/protein ratio, but also on the Vero-protein impurity. With comparable infection times, comparable yields could be obtained with a significantly improved impurity profile.

Example 4

Influenza A/Panama/2007/99 Production with Early Virus Amplification at 35° C.

To confirm the behavior observed in Example 3 for the two-temperature process, the same temperature profiles were used for propagating Influenza A/Panama/2007/99 virus in 100 liter Vero cultures. All other conditions and parameter sets according to Example 3.

In Table 5, Influenza A/Panama/2007/99 antigen purity (SRD/protein ratio) and Vero-protein impurity of the sucrose gradient purified virus from the 100 liter scale runs are compared.

TABLE 5

Comparison of Influenza A/Panama/2007/99antigen purity (SRD/protein ratio) and Vero-protein impurity. The virus was purified from temperature experiments using a sucrose gradient.

| Production conditions | Yield (mg SRD/l harvest) | SRD/Protein Ratio (mg/mg) | Vero-protein/SRD Ratio (mg/mg) |
|---|---|---|---|
| 32° C. until 88 hrs. p.i. | 2.3 | 0.31 | 0.84 |
| 35° C. until 24 hrs. p.i./ 32° C. until 67 hrs. p.i. | 1.9 | 0.45 | 0.11 |

The production of A/Panama/2007/99 virus at 35° C. during the first 24 hours of virus replication and subsequent reduction of the temperature to 32° C. has several advantages over the current processing at a constant temperature of 32° C. In general, the quality of the Influenza virus antigen can be improved, as evidenced by the ratios of SRD/protein and Vero-protein/SRD. With a significantly reduced infection time the yields were slightly lower, but the impurity profile especially for the relative amount of Vero cell protein is significantly better.

Influenza virus antigen purity is a factor in the manufacturing of influenza vaccines. It is generally accepted that, for the replication of Influenza viruses in Vero cells, the proteolytic conditions for the cleavage of the precursor hemagglutinin and the appropriate temperature conditions are some of the important factors. In the exemplary experiments presented herein, it was demonstrated that a temperature profile having an elevated temperature during the early phase of virus replication resulted in an improved antigen at the sucrose gradient step. In addition, the production of Influenza virus at 35° C. for the first 24 hours corresponded to better process performance with respect to cycle time. Influenza A/Panama/2007/99 and A/New Caledonia/20/99 were used as model systems to prove the usefulness of two-temperature virus propagation. Results from culture experiments performed in the 10 and 100 liter scale therefore indicate the benefits in changing from 32° C. to 35° C. for about the first 24 hours of the virus propagation process.

Example 5

Influenza A/Hiroshima/52/2005 Production with Early Virus Amplification at 35° C. for 18 hrs. p.i. vs. 36 hrs. p.i. Followed by 32° C. Until End of Virus Propagation This example shows the effect of varying the duration of the high-temperature cycle on the antigen yield, SRD/protein ratio, and Vero protein/SRD ratio for 50 L Vero cultures infected with Influenza A/Hiroshima/52/2005 virus. For two separate samples, a temperature of 35° C. was maintained for 18 hrs. p.i. and 36 hrs. p.i., respectively, before reducing the temperature to 32° C. Virus-containing supernatants were harvested, inactivated and purified by ultracentrifugation.

In Table 6, Influenza A/Hiroshima/52/2005 antigen purity (SRD/protein ratio) and Vero-protein impurity of the sucrose gradient purified virus from the 50 liter scale runs are compared.

TABLE 6

Comparison of Influenza A/Hiroshima/52/2005 antigen yield, purity (SRD/protein ratio) and Vero-protein impurity. The virus was purified from temperature experiments using a sucrose gradient.

| Production conditions | Yield (mg SRD/l harvest) | SRD/Protein Ratio (mg/mg) | Vero-protein/ SRD ratio (mg/mg) |
|---|---|---|---|
| 35° C. for 18 hrs. p.i./32° C. until end (58 hrs. p.i.) | 3.7 | 1.16 | 0.02 |
| 35° C. for 36 hrs. p.i./32° C. until end (58 hrs. p.i.) | 4.8 | 1.12 | 0.02 |

The production of Influenza A/Hiroshima/52/2005 virus at 35° C. for 18 hrs. and 36 hrs. p.i. respectively resulted in comparable yields and purity profiles (Table 6). From these results, it can be concluded that the duration of increased temperature during early virus propagation and the duration of reduced temperature until harvest can be widely varied in a dual temperature profile.

Example 6

Influenza B/Malaysia/2506/2004 Production with Different Temperatures (34° C., 35° C. and 36° C.) for Early Virus Amplification for 18 hrs. p.i. Followed by a 3° C. Reduction (to 31° C., 32° C. and 33° C.) Until End of Virus Propagation This Example concerns the use of different dual temperature profiles during virus propagation in 32 liter to 80 liter Vero cultures that were infected with Influenza B/Malaysia/2506/2004 virus. Higher temperatures of 34° C., 35° C. and 36° C. were maintained for 18 hrs. p.i. before reduction by 3° C., respectively, to 31° C., 32° C., and 33° C. Virus containing supernatants were harvested, inactivated and purified by ultracentrifugation.

In Table 7, Influenza B/Malaysia/2506/2004 antigen yield, purity (SRD/protein ratio) and Vero-protein impurity of the sucrose gradient purified virus from the 32 liter to 80 liter scale runs are compared for the different temperature profiles.

TABLE 7

Comparison of Influenza B/Malaysia/2506/2004 antigen yield, purity (SRD/protein ratio) and Vero-protein impurity. The virus was purified from temperature experiments using a sucrose gradient.

| Production conditions | Yield (mg SRD/l harvest) | SRD/Protein Ratio (mg/mg) | Vero-protein/ SRD ratio (mg/mg) |
|---|---|---|---|
| 36° C. for 18 hrs. p.i./33° C. until end (69 hrs. p.i.) (32 L bioreactor) | 7.3 | 0.31 | 0.06 |
| 35° C. for 18 hrs. p.i./32° C. until end (70 hrs. p.i.) (80 L bioreactor) | 8.0 | 0.39 | 0.05 |
| 34° C. for 18 hrs. p.i./31° C. until end (70 hrs. p.i.) (32 L bioreactor) | 7.3 | 0.36 | 0.04 |

The production of Influenza B Malaysia/2506/2004 virus at 34° C. to 36° C. for 18 hrs. p.i. followed by a 3° C. reduction until end of virus propagation resulted in comparable yields and purity profiles (Table 7). From these results, it can be concluded that the range of increased temperature during early virus propagation and the range of reduced temperature until time of harvest can be widely varied in a dual temperature profile.

Example 7

Influenza A/Solomon Islands/3/2006 Production with Different Temperatures (33.5° C., 35° C. and 36.5° C.) for Early Virus Amplification for 18 hrs. p.i. Followed by a 3° C. Reduction (to 30.5° C., 32° C. and 33.5° C.) Until End of Virus Propagation This example concerns the use of different temperature profiles during virus propagation in 32 liter to 50 liter Vero cultures infected with Influenza A/Solomon Islands/3/2006 virus. Higher temperatures of 33.5° C., 35° C. and 36.5° C. were maintained for 18 hrs. p.i. before reduction by 3° C., respectively, to 30.5° C., 32° C. and 33.5° C. Virus containing supernatants were harvested, inactivated and purified by ultracentrifugation.

In Table 8, Influenza A/Solomon Islands/3/2006 antigen yield, purity (SRD/protein ratio) and Vero-protein impurity of the sucrose gradient purified virus from the 32 liter to 50 liter scale runs are compared.

TABLE 8

Comparison of Influenza A/Solomon Islands/3/2006 antigen yield, purity (SRD/protein ratio) and Vero-protein impurity. The virus was purified from temperature experiments using a sucrose gradient.

| Production conditions | Yield (mg SRD/l harvest) | SRD/Protein Ratio (mg/mg) | Vero-protein/ SRD ratio (mg/mg) |
|---|---|---|---|
| 36.5° C. for 18 hrs. p.i./33.5° C. until end (54 hrs. p.i.) (32 L bioreactor) | 4.0 | 0.53 | 0.05 |
| 35° C. for 18 hrs. p.i./32° C. until end (55 hrs. p.i.) (50 L bioreactor) | 3.2 | 0.72 | 0.03 |
| 33.5° C. for 18 hrs. p.i./30.5° C. until end (69 hrs. p.i.) (50 L bioreactor) | 3.0 | 0.74 | 0.02 |

The production of Influenza A/Solomon Islands/3/2006 virus at 33.5° C., 35° C., and 36.5° C. for 18 hrs. p.i. followed by a 3° C. reduction, respectively, until end of virus propagation resulted in comparable yields and purity profiles (Table 8). Higher yields at elevated temperatures also resulted in reduced purity, however these impurities remain at relatively low levels with the 3° C. reduction at the end of virus propagation. With dual temperature profiles having reduced temperatures (e.g. 33.5° C./30.5° C.) comparable yields can be achieved, however longer cycle times of virus propagation (which are still below 70 hrs) are needed to reach these comparable yields. Purity profiles, especially host cell specific Vero-protein, are typically improved with the lower temperature range including a 3° C. temperature shift (see also Table 7 with B/Malaysia at 34° C./31° C.). From these results, it can be concluded that, for both Influenza A and B strains, the range of increased temperature during early virus propagation and the range of reduced temperature until time of harvest can be widely varied in a dual temperature profile.

Example 8

Ross River Virus Production

Ross River Virus ("RRV") was produced in 2 L reactors at different temperatures. The investigated temperatures were 37° C., 35° C., 32° C. and 35° C. for 30 hrs. and 32° C. after 30 hrs until end of infection after 90 hrs. p.i. Kinetic parameters were determined and samples were collected at the following time intervals (in hrs) I-18, I-42, I-42, I-54, I-66, I-76 and I-90. Samples for NaBr analysis were treated with 20 µL/mL formalin 1.85% and incubated for 48 hrs at 37° C. Residual Oxygen Uptake Rates (OUR) were measured during the virus propagation to monitor the metabolic activity of the infected cells. Cell detachment rates were quantified by microscopic images of the microcarrier cultures. The TCID50 (50% Tissue Culture Infective Dose) was also determined.

Conditions were at pH 7.1 PBS and 20% $pO_2$, 1.0 g/L glucose prior infection. At I-18 1.0 g/L glucose were added and perfusion stopped. After I-42 glucose was added if glucose decreased lower than 1.0 g/L. The results are shown in Table 9.

TABLE 9

| | glucose [g/L] | HA [HAU/ 50 µL] | TCID50 [log/mL] | OD 254 nm [nm] | OD 610 nm [nm] | cell detachment [%] | Residual OUR [%] | peak height [1/10 breadth] |
|---|---|---|---|---|---|---|---|---|
| RRV 37° C. | | | | | | | | |
| I-18 | 2.20 | 5 | 6.68E07 | | | 11.2 | | |
| I-42 | 1.65 | 8 | 1.46E09 | | | 100 | | |
| I-53 | 1.38 | 7 | 1.20E09 | 6.273 | 0.0158 | 100 | 50 (±10%) | 6.5 |
| I-66 | 1.21 | 8 | 1.95E09 | 5.993 | 0.0113 | 100 | 15 (±5%) | 4.5 |
| I-76 | 1.27 | 7 | 4.12E07 | 5.597 | 0.0260 | 100 | 2 | 5 |
| I-90 | 1.25 | 7 | 6.68E06 | 5.811 | 0.0136 | 100 | 0 | 7 |
| RRV 35° C. | | | | | | | | |
| I-18 | 2.38 | 4 | 1.46E08 | | | 18 | | |
| I-42 | 1.90 | 7 | 1.95E09 | | | 100 | | |
| I-53 | 1.95 | 6 | 4.37E08 | 5.894 | 0.0125 | 100 | 55 (±10%) | 5.5 |
| I-66 | 1.63 | 7 | 1.46E08 | 7.187 | 0.0131 | 100 | 30 (±5%) | 4 |
| I-76 | 1.72 | 7 | 1.10E08 | 5.942 | 0.0198 | 100 | 6 | 5 |
| I-90 | 1.71 | 7 | 1.62E07 | 6.570 | 0.0160 | 100 | 0 | 2 |
| RRV 32° C. | | | | | | | | |
| I-18 | 2.55 | 2 | 1.20E07 | | | 2 | | |
| I-42 | 2.35 | 8 | 3.12E09 | | | 14 | | |
| I-53 | 1.81 | 7 | 5.18E09 | 5.777 | 0.0118 | 49 | 75 (±10%) | 7 |
| I-66 | 1.43 | 8 | 2.68E09 | 5.601 | 0.0107 | 100 | 50 (±5%) | 3.5 |
| I-76 | 1.28 | 7 | 1.10E09 | 6.230 | 0.0173 | 100 | 20 | 7.5 |
| I-90 | 1.13 | 6 | 6.68E08 | 5.042 | 0.0139 | 100 | 6 | 7 |
| RRV 35/ 32° C. | | | | | | | | |
| I-18 | 2.42 | 5 | 8.86E07 | | | 7 | | |
| I-42 | 2.32 | 8 | 3.08E09 | | | 25 | | |
| I-53 | 1.89 | 8 | 4.37E09 | 5.540 | 0.0138 | 97 | 60 (±10%) | 8 |

TABLE 9-continued

| | | | | | | | | |
|---|---|---|---|---|---|---|---|---|
| I-66 | 1.68 | 8 | 4.12E09 | 5.991 | 0.0109 | 100 | 50 (±5%) | 5.5 |
| I-76 | 1.51 | 8 | 2.67E09 | 6.513 | 0.0212 | 100 | 25 | 8 |
| I-90 | 1.41 | 6 | 8.86E07 | 5.453 | 0.0622 | 100 | 5 | 7 |

Centrifugation conditions:
I-18: 5000 g
I-42-I-66: 10000 g
I-78-I-90: 15000 g

The NaBr plot of all four incubations is given in FIGS. 2 to 5 in 4 intervals (A: 54 h, B: 66 h, C: 78 h, D: 90 h).

Figure 6:
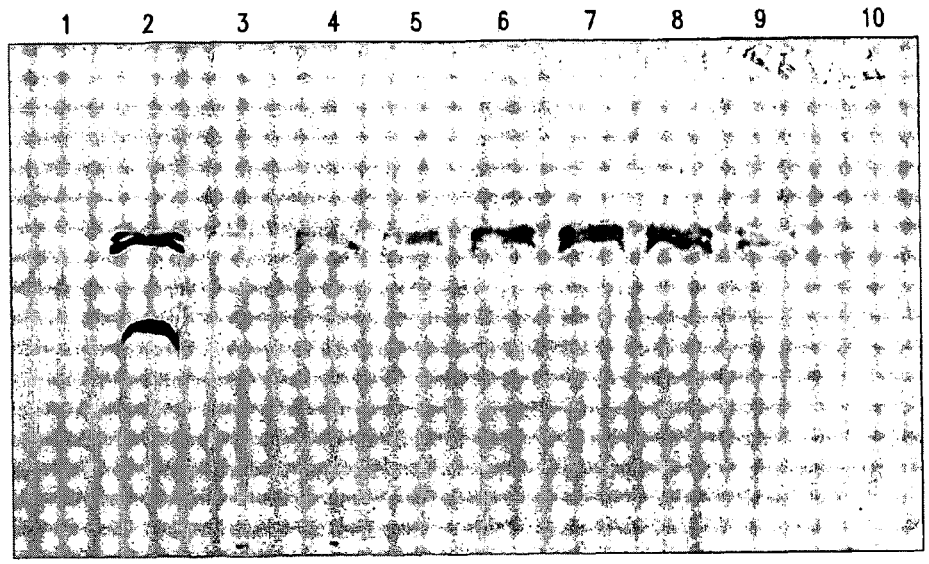
FIG. 6: western blots of Ross River Virus inoculum of infections at 37° C. and 35° C./32° C.
Figure 7A:
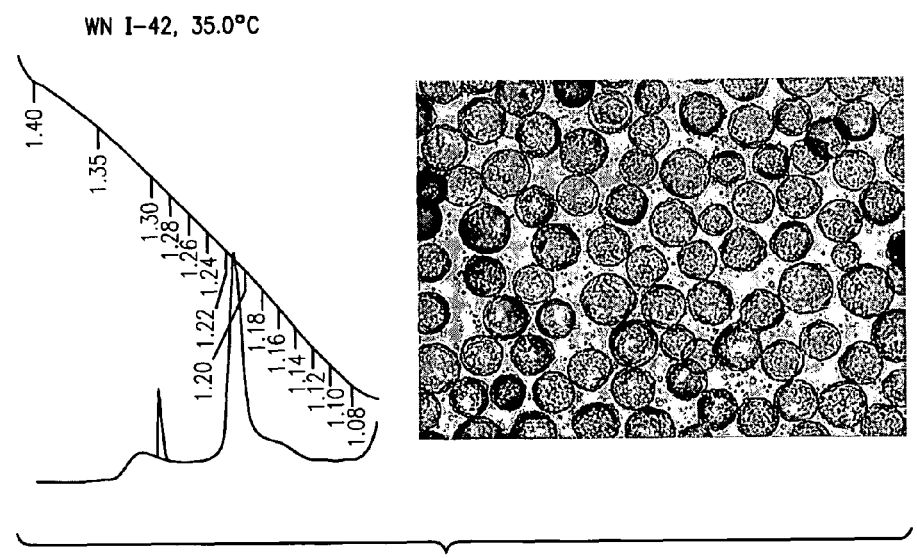
FIG. 7: NaBr plot of West Nile Virus infection at 35° C. at various time points after infection, with microscopic images.
Figure 7B:
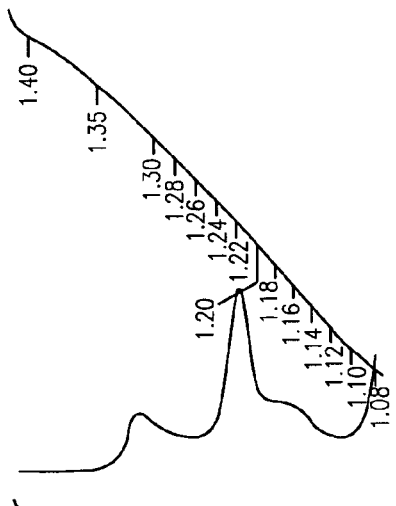
Figure 7B:
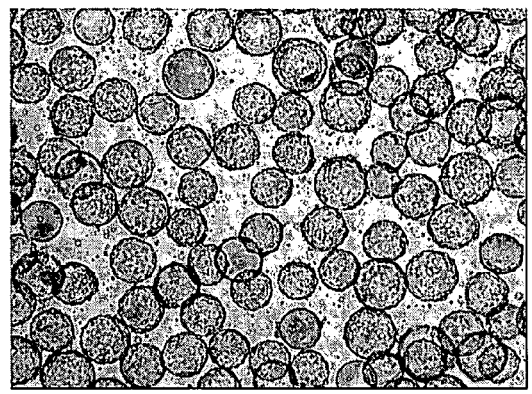
Figure 7C:
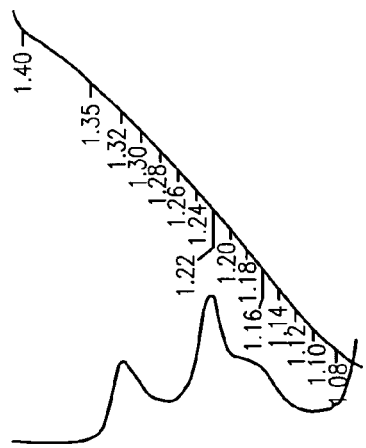
Figure 7C:
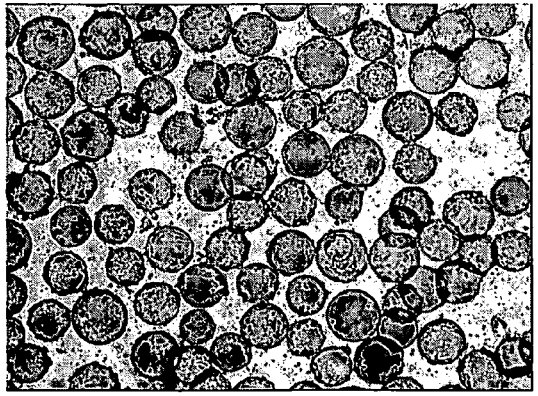
Figure 7D:
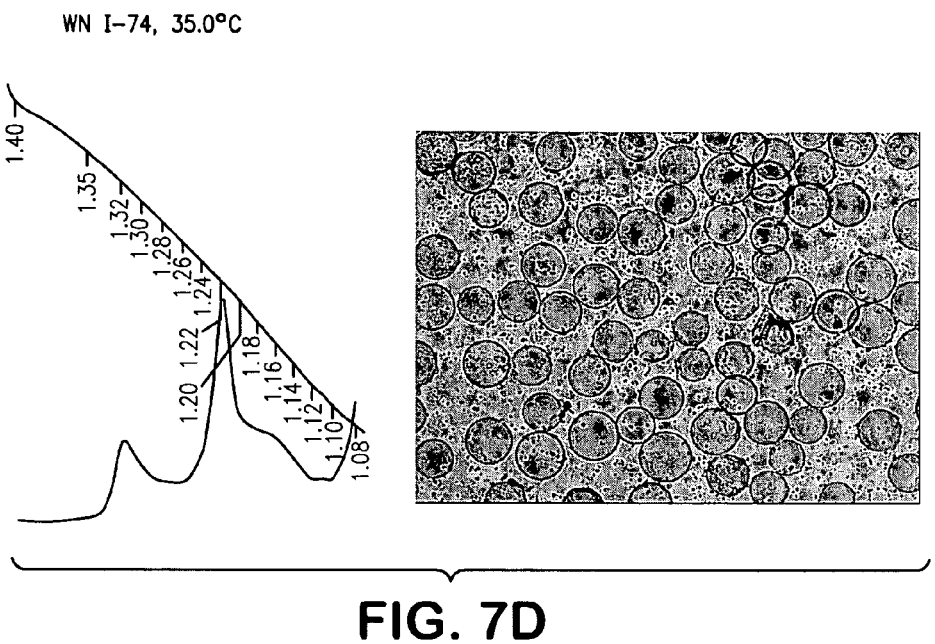
Figure 8A:
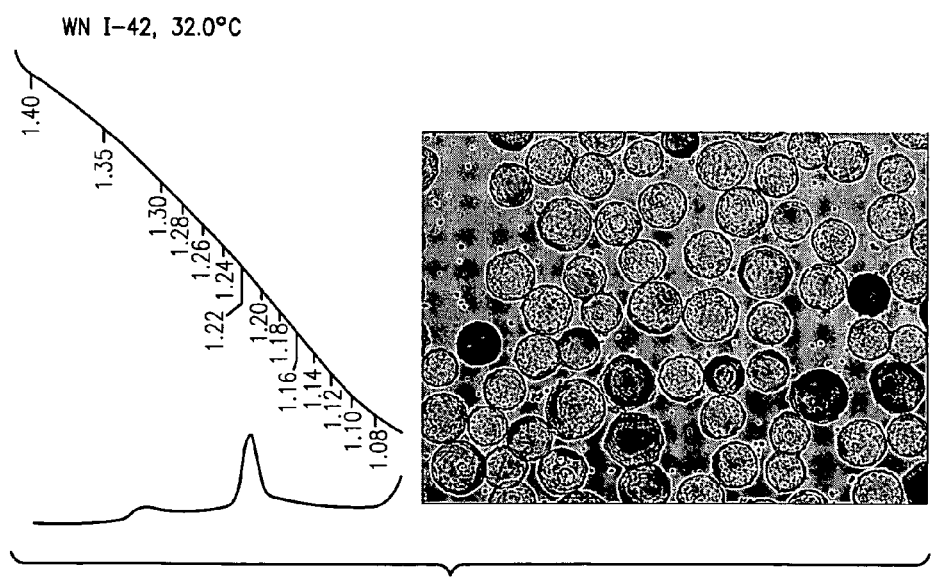
FIG. 8: NaBr plot of West Nile Virus infection at 32° C. at various time points after infection, with microscopic images.
Figure 8B:
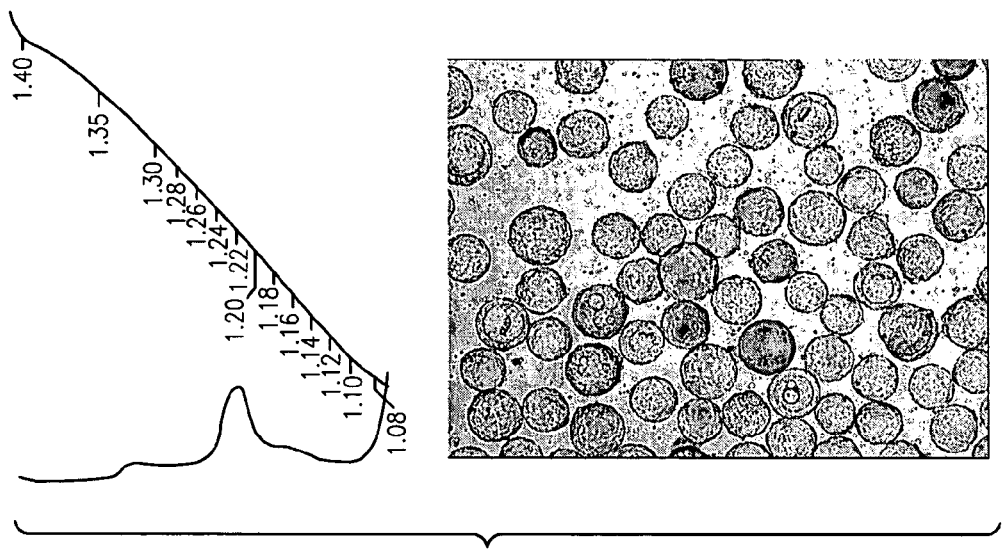
Figure 8C:
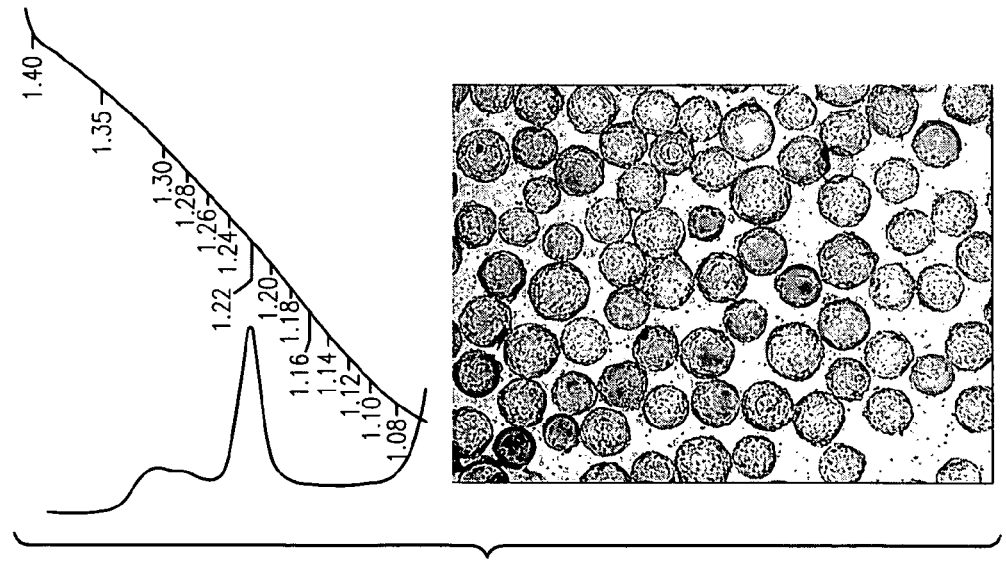
Figure 8D:
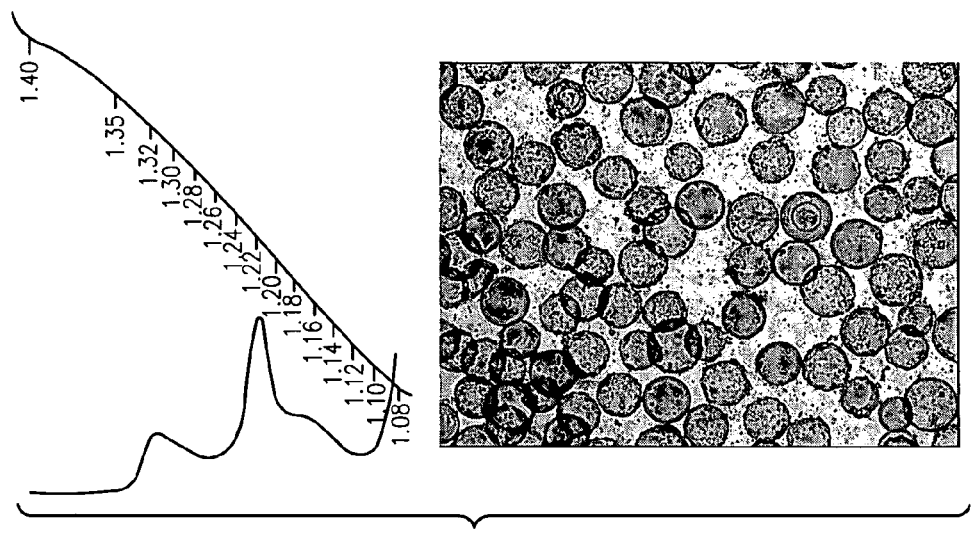
Figure 9A:
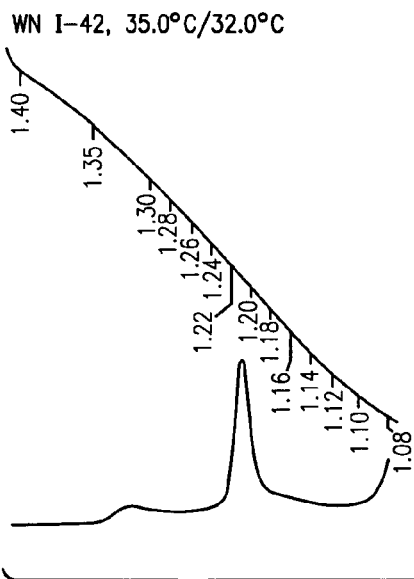
FIG. 9: NaBr plot of West Nile Virus infection at 35° C./32° C. at various time points after infection, with microscopic images.
Figure 9B:
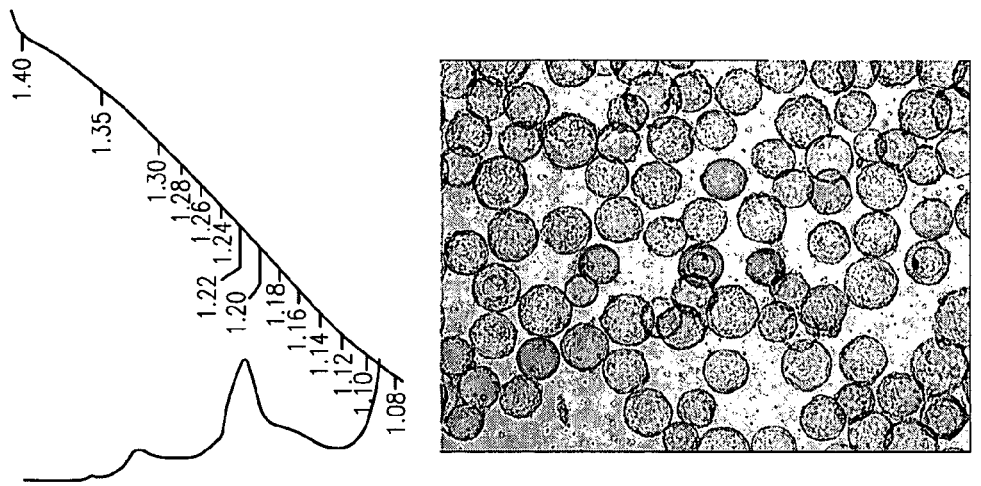
Figure 9C:
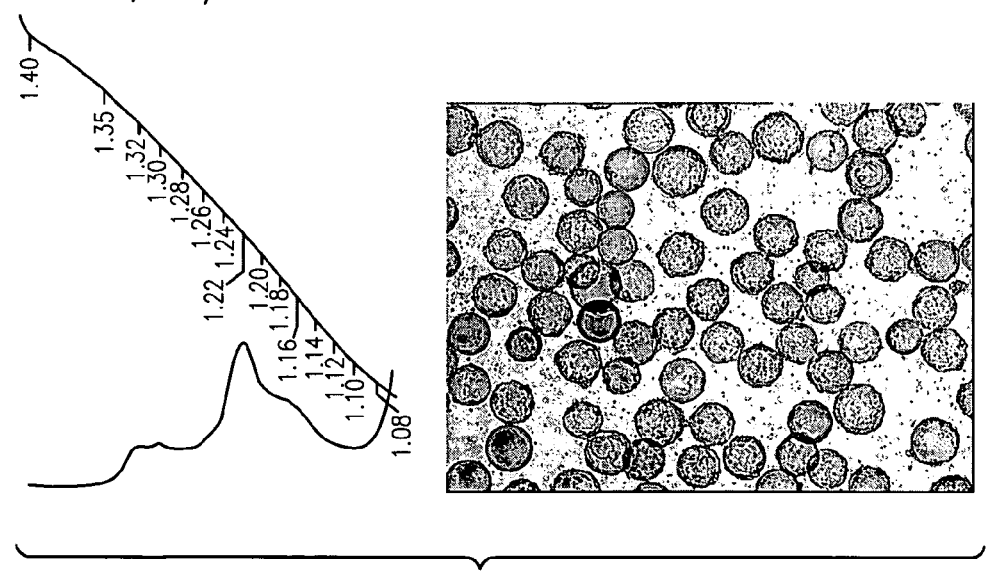
Figure 9D:
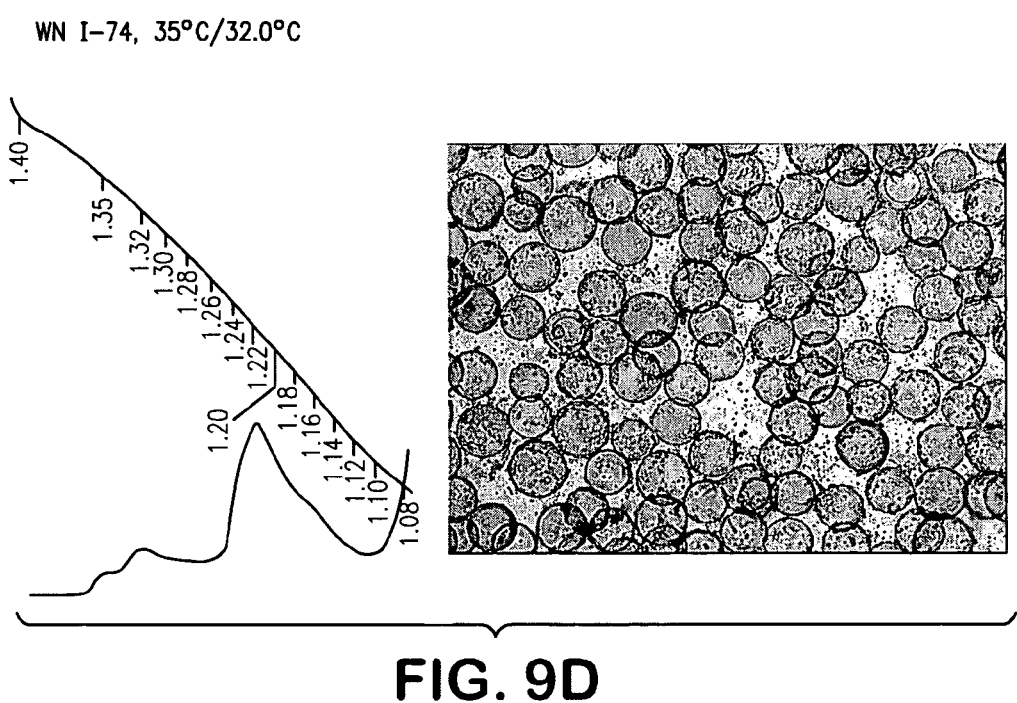

Western blots were performed with the following antibodies: (1)RR (ATCCVR373), Hyperimmune Ascites Fluid, Mouse; N.I.H. (1:1000), and (2) anti-mouse IgG, Sigma, Cat#: A-4656, Lot#: 63H8830 (1:5000). Results are given in FIG. 6 according to Table 10.

TABLE 10

| Lane | Probe | volume [µL] |
|---|---|---|
| 1 | marker | 10 |
| 2 | RRV Positive control | 20 |
| 3 | RRV 37° C. I-54 | 20 |
| 4 | RRV 37° C. I-66 | 20 |
| 5 | RRV 37° C. I-78 | 20 |
| 6 | RRV 35° C./32° C. I-54 | 20 |
| 7 | RRV 35° C./32° C. I-66 | 20 |
| 8 | RRV 35° C./32° C. I-78 | 20 |
| 9 | RRV 35° C./32° C. I-90 | 20 |
| 10 | negative control (pellet) | 20 |

At both high temperature inoculations (37° C. and 35° C.) infection kinetics were considerably increased with 100% cell detachment rate after 42 hrs and ca. 50% residual $O_2$ after 53 hrs. The approaches with lower temperature (32° C. and 35° C./32° C.) were comparatively slower. This is also apparent in the titer analysis at I-18. However, after I-42 all approaches reached ca. 1E09 TCID50/mL. The approaches with a lower temperature showed a more stable titer (>1E09 TCID50/mL until I-76) near the end of the infection. Until I-76 in both approaches, a residual OUR of 20% could be measured. In all experiments after I-53, the maximal peak height in the NaBr-gradient was reached, whereas a lower peak was measured for all I-66 samples as well as I-90 in the 35° C. inoculation. Because of the increased temperature, the glucose levels fell faster during the 37° C. and 35° C. experiments. Because of increased infection kinetic no metabolic activity is determinable afterwards. In all experiments the glucose levels were similar at the end.

A fast virus propagation at the beginning and a stable titer until end of infection was established only during the two phase temperature experiment (35° C. until I-30, then 32° C.). Under these conditions, the highest peaks were measured in the NaBr gradient experiment which are stable until I-78. Also in the western blot more stable bands were detected for the 35° C./32° C. experiment.

Example 9

West Nile Virus Experiments

West Nile Virus was produced in 2 L reactors at different temperatures. The investigated temperatures were 35° C., 32° C. and 35° C. for 30 hrs and 32° C. after 30 hrs until end of infection. Kinetic parameters were collected for 90 h. Samples were collected at the following time intervals (in hrs) I-18, I-30, I-42, I-42, I-52, I-66, I-74 and I-90. Samples for NaBr analysis were treated with 20 µL/mL formalin 1.85% and incubated for 48 hrs at 37° C. Conditions were at pH 7.1, 20% $pO_2$, and 1.0 g/L glucose prior infection. At I-18 1.0 g/L glucose were added and perfusion stopped. Results are given in Table 11 and FIGS. 7-9 show NaBr plots and microscopic images. Cell detachment rates were quantified by these microscopic images of the microcarrier cultures

TABLE 11

| | Glucose [g/L] | TCID50 [log/mL] | Residual formalin [µg/mL] | Cell detachment [%] |
|---|---|---|---|---|
| WN 35.0° C. | | | | |
| I-18 | 2.18 | 8.86E+07 | | 14.9 |
| I-30 | 2.75 | 1.46E+09 | 116 | 12.9 |
| I-42 | 0.94 | 1.20E+10 | 137 | 32.9 |
| I-52 | 0.21 | 6.68E+09 | 119 | 80.6 |
| I-66 | 0.24 | 8.86E+09 | 127 | 98.4 |
| I-74 | 0.00 | 3.12E+09 | 125 | 100.0 |
| I-90 | 0.11 | 6.68E+06 | 130 | 100.0 |
| WN 32° C. | | | | |
| I-18 | 2.37 | 5.16E+06 | | 17.9 |
| I-30 | 3.37 | 1.62E+08 | 127 | 9.9 |
| I-42 | 2.34 | 5.18E+09 | 136 | 21.9 |
| I-52 | 1.43 | 4.12E+09 | 117 | 26.9 |
| I-66 | 0.22 | 8.86E+09 | | 81.6 |
| I-74 | 0.00 | 1.20E+10 | 116 | 92.9 |
| I-90 | 0.37 | 6.38E+09 | 135 | 100.0 |
| WN 35° C./32° C. | | | | |
| I-18 | 2.12 | 5.18E+06 | | 20.5 |
| I-30 | 2.80 | 1.95E+09 | 118 | 13.9 |
| I-42 | 1.56 | 1.10E+10 | 141 | 18.9 |
| I-52 | 0.55 | 8.86E+09 | 118 | 35.0 |
| I-66 | 0.00 | 8.86E+09 | 127 | 94.9 |
| I-74 | 0.00 | 6.68E+09 | | 100.0 |
| I-90 | 0.19 | 1.46E+08 | | 100.0 |

What is claimed is:

1. A method for the production of a virus, the method comprising cultivating a host cell at a cell culture propagation temperature;

infecting the host cell with a virus to form an infected host cell;

cultivating the infected host cell at a first temperature in the range from 30° C. to 37.5° C. for 1 to 48 hours, wherein the first temperature is less than the cell culture propagation temperature;

subsequently cultivating the infected host cell at a second temperature which is 1° C. to 6° C. less than the first temperature, and collecting copies of the virus produced by the cultivation steps.

2. The method according to claim 1, wherein said virus is an orthomyxovirus, alphavirus or flavivirus.

3. The method of claim 2, wherein said virus is an influenza virus.

4. The method of claim 3, wherein said virus is selected from influenza A and B.

5. The method of claim 2, wherein said virus is Ross River Virus.

6. The method of claim 2, wherein said virus is West Nile Virus.

7. The method of claim 1, wherein said host cell is of an animal cell culture or cell line.

8. The method of claim 7, wherein said host cell is an epithelial cell.

9. The method of claim 8, wherein said host cell is a kidney epithelial cell.

10. The method of claim 9, wherein said host cell is a Vero cell.

11. The method of claim 1, wherein said first temperature ranges from 32° C. to 37° C.

12. The method of claim 11, wherein said first temperature ranges from 33° C. to 36° C.

13. The method of claim 12, wherein said first temperature ranges from 34° C. to 35.5° C.

14. The method of claim 1, wherein said second temperature is decreased by 1.5° C. to 5° C. compared to said first temperature.

15. The method of claim 14, wherein said second temperature is decreased by 2° C. to 4° C. with respect to said first temperature.

16. The method of claim 1, wherein said second temperature ranges from 29° C. to 35° C.

17. The method of claim 16, wherein said second temperature ranges from 30° C. to 34° C.

18. The method of claim 17, wherein said second temperature ranges from 31° C. to 33° C.

19. The method of claim 1, wherein said host cell is cultivated directly after inoculation.

20. The method of claim 1 further comprising the step of isolating said virus or viral antigens from said virus.

21. The method of claim 20, further comprising the step of fragmenting said virus.

22. The method of claim 20, further comprising the step of inactivating the virus.

23. The method of claim 1, further comprising the step of preparing an immunogenic composition with said virus.

24. The method of claim 1, wherein said cultivation at a first temperature is for at least two hours.

25. The method of claim 1, wherein said cultivation at a second temperature is for 24 to 67 hours.

* * * * *